United States Patent [19]

Ishiguro et al.

[11] Patent Number: 4,851,105

[45] Date of Patent: Jul. 25, 1989

[54] OXYGEN SENSING ELEMENT AND METHOD FOR PRODUCING THE SAME

[75] Inventors: Fujio Ishiguro; Takumi Narahara, both of Nagoya, Japan

[73] Assignee: NGK Insulators, Ltd., Nagoya, Japan

[21] Appl. No.: 154,307

[22] Filed: Feb. 10, 1988

[30] Foreign Application Priority Data

Feb. 16, 1987 [JP] Japan .................................. 62-32931

[51] Int. Cl.$^4$ ............................................. G01N 27/58
[52] U.S. Cl. ...................................... 204/429; 427/123
[58] Field of Search ................... 204/429, 15; 427/123

[56] References Cited

U.S. PATENT DOCUMENTS

| | | | |
|---|---|---|---|
| 3,607,433 | 9/1971 | Isenberg et al. | 427/115 |
| 4,356,065 | 10/1982 | Dietz | 204/1 T |
| 4,359,374 | 11/1982 | Sano et al. | 204/429 |
| 4,477,487 | 10/1984 | Kojima et al. | 427/123 |

FOREIGN PATENT DOCUMENTS 2711880 9/1978 Fed. Rep. of Germany .

Primary Examiner—G. L. Kaplan
Attorney, Agent, or Firm—Arnold, White & Durkee

[57] ABSTRACT

An oxygen sensing element adapted primarily to determine an oxygen partial pressure of a measurement gas, including a solid electrolyte body having a surface, at least a portion of which is undulated. An electrode is formed on the undulated portion of the surface of the solid electrolyte body. The electrode is covered by a porous protective coating, such that the electrode is exposed to the measurement gas through the porous protective coating. The undulated portion of the solid electrolyte body has an average height of at least 50 microns between the top and bottom of its convexed and concaved parts. At least a portion of the porous protective coating is positioned within at least one of the concaved parts of the undulated portion of the solid electrolyte body. A method of producing the instant sensing element is also disclosed.

9 Claims, 2 Drawing Sheets

| OPERATING TIME (hr) | | 0 | 250 | 500 | 750 | 1000 |
|---|---|---|---|---|---|---|
| WITHOUT UNDULATED PORTION | 1 | | | | ✕ | |
| | 2 | | | ✕ | | |
| | 3 | | | | | ✕ |
| | 4 | | | ✕ | | |
| | 5 | | | | | ○ |
| | 6 | | | | | ○ |
| | 7 | | | | | ✕ |
| WITH UNDULATED PORTION (50~60μm) | 1 | | | | | ○ |
| | 2 | | | | | ○ |
| | 3 | | | | | ○ |
| | 4 | | | | | ○ |
| | 5 | | | | | ○ |
| | 6 | | | | | ○ |
| | 7 | | | | | ○ |

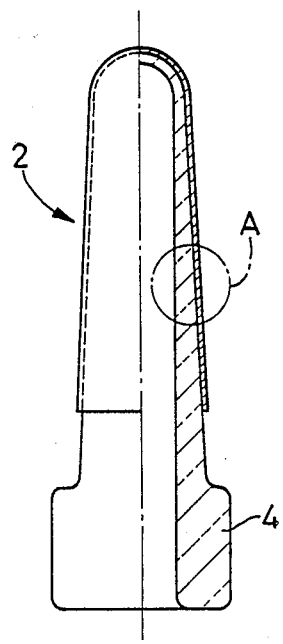
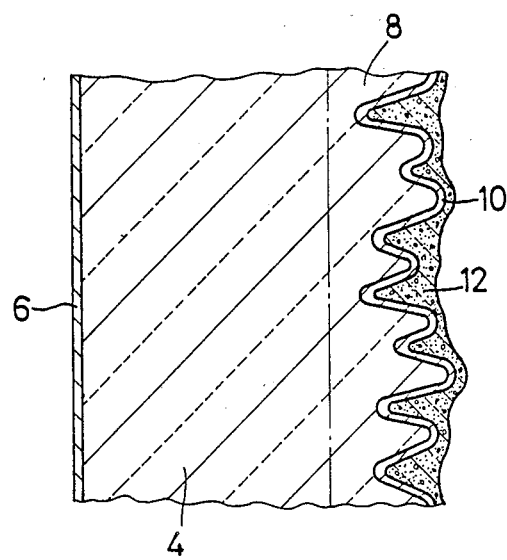
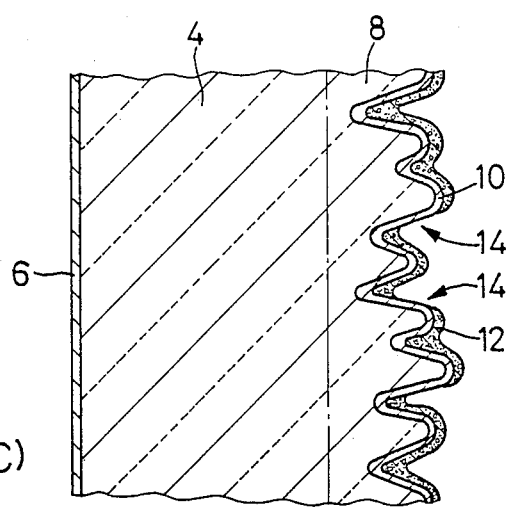

OXYGEN SENSING ELEMENT AND METHOD FOR PRODUCING THE SAME

BACKGROUND OF THE INVENTION

1. Field of the Invention

The present invention relates generally to an oxygen sensor for determining an oxygen concentration in exhaust gases such as those emitted by internal combustion engines and boilers, and a method of producing such an oxygen sensor. More particularly, the invention is concerned with a technique useful for improving the durability of such an oxygen sensor.

2. Discussion of the Prior Art

In the art of controlling an air/fuel (A/F) ratio or burning condition of an air-fuel mixture supplied to automotive internal combustion engines, boilers or other equipment, it is known to detect the oxygen concentration of exhaust gases emitted by such engines or boilers, by utilizing a sensor which uses an oxygen-ion conductive solid electrolyte such as zirconia ceramics. The sensor is operated according to the principle of an oxygen concentration cell.

Such an oxygen sensor for detecting the oxygen concentration employs a sensing element which includes a tubular solid electrolyte body which is closed at one of its opposite ends and open at the other end. The solid electrolyte body has an inner and an outer electrode formed on its respective inner and outer surfaces. The inner electrode serves as a reference electrode which is exposed to ambient air as a reference gas having a known oxygen concentration. On the other hand, the outer electrode serves as a measuring electrode which is exposed to a measurement gas in the form of the exhaust gases emitted by an internal combustion engine. According to this oxygen sensor, the concentration of oxygen in the exhaust gases is determined by measuring an electromotive force that is induced between the reference and measuring electrodes, based on a difference in the oxygen concentration between the reference gas and the measurement gas.

In a known oxygen sensor of the type described above, an oxygen-ion conductive solid electrolyte constitutes a suitably shaped main body of the oxygen sensing element, on which the electrodes are formed in contact with the surfaces of the solid electrolyte. In operation, the measuring electrode formed on the outer surface of the solid electrolyte main body is subject to heat of the exhaust gases having a generally high temperature. Consequently the measuring electrode tends to suffer from thermal wear or damage, and the sensing capability or measuring accuracy of the oxygen sensor is deteriorated. To solve this problem, it has been proposed to protect the measuring electrode from direct exposure to the exhaust gases by covering the measuring electrode with a porous protective coating having a suitable thickness, which is formed by plasma-spraying spinel or other ceramic material over the measuring electrode.

However, the protective coating formed on the sensing element of the oxygen sensor suffers from separation or peel-off from the surface of the solid electrolyte main body, due to repetitive thermal expansion and contraction caused by an excessively large change in the environmental temperature of the sensor during its use while being attached to the exhaust pipe of an automotive engine, for example. To alleviate ths problem, it has been proposed to increase the adhesive strength of the protective coating relative to the solid electrolyte main body. This requires an increased amount of energy to effect a plasma-spraying of the appropriate ceramic material to the main body. In this case, however, the protective coating tends to be too dense to permit easy permeation of the measurement gas therethrough, leading to an extremely low operating response of the sensing element. Further, such a relatively dense protective coating may be readily clogged by fine particles of iron, phosphorus, zinc or other substances contained in the measurement gas. This also leads to the deterioration of the operating response of the oxygen sensor.

On the other hand, there has been proposed another technique to improve the adhesion between the measuring electrode and the solid electrolyte main body. An example of this technique is disclosed in U.S. Pat. No. 4,477,487 and German Patent No. 3118299, wherein the measuring electrode is disposed on an undulated outer layer of a solid electrolyte formed as an integral outer part of the main body of the sensing element. The adhesive strength between the electrode and the main body is increased owing to an increased area of contact therebetween, due to the engagement of the electrode with the relatively short-pitched convexed and concaved portions of the undulated outer layer of the main body. To further improve the durability of the measuring electrode thus formed on the undulated surface portions of the main body, it is attempted to utilize the above-indicated technique to apply a porous ceramic protective coating to the measuring electrode, to protect the measuring electrode.

In the oxygen sensing element with its measuring electrode formed on its undulated outer surface and covered by the protective coating, as described above, the measuring electrode still suffers from a problem, that is, deterioration, evaporation or expansion due to its exposure to high-temperature exhaust gases. This thermal problem may often cause peel-off or separation of the protective coating due to an expanding force of the electrode acting on the protective coating. Thus, the above-indicated known sensing element is not completely satisfactory, in terms of the durability of the protective coating.

SUMMARY OF THE INVENTION

It is therefore an object of the present invention to provide an oxygen sensing element which overcomes the problem discussed above, and which is particularly resistant to deterioration of its operating response and is excellent in the anti-peel-off durability of its protective coating which covers the measuring electrode.

Another object of the invention is to provide a method suitable for producing such an improved oxygen sensing element.

According to one aspect of the present invention, there is provided an oxygen sensing element adapted primarily to determine an oxygen partial pressure of a measurement gas, comprising: a solid electrolyte body formed of an oxygen-ion conductive solid electrolyte material, and having a surface at least a portion of which is undulated, the undulated portion having convexed and concaved parts; an electrode formed on the undulated portion of the surface of the solid electrolyte body; and a porous protective coating covering the electrode, such that the electrode is exposed to the measurement gas through the porous protective coating. The undulated portion of the solid electrolyte body has an average height of at least 50 microns between the convexed and concaved parts. Further, at least a portion of the porous protective coating is positioned within at least one of the concaved parts of the undulated portion of the solid electrolyte body.

According to one preferred feature of the oxygen sensing element of the instant invention, the electrode formed on the undulated portion of the solid electrolyte body has at least one exposed area which is left uncovered by the porous protective coating, so that the uncovered portion is directly exposed to the measurement gas. Each exposed area of the electrode may be provided on one of two flanks of the corresponding convexed part of the undulated portion of the solid electrolyte body, or on the bottom of the corresponding concaved part of the undulated portion.

The oxygen sensing element of the invention may be suitably produced by a method provided according to another aspect of the invention, which method comprises the steps of: preparing an unfired formed body that gives by firing thereof the solid electrolyte body, or alternatively a calcined formed body that is obtained by firing the unfired formed body at a temperature lower than a firing temperature of the unfired formed body, the unfired or calcined formed body being formed such that an undulated portion having convexed and concaved parts is formed at least in a portion of an area of the surface of the formed body on which an electrode is formed; firing the unfired or calcined formed body into the solid electrolyte body so that the undulated portion has an average height of at least 50 microns between the top of the convexed parts and the bottom of the concaved parts; forming the electrode on the above-indicated area of the surface of the prepared solid electrolyte body, which area includes the above-indicated undulated portion; and forming a porous protective coating so as to cover the electrode, such that at least a portion of the protective coating is positioned within at least one of the concaved parts of the undulated portion of the solid electrolyte body.

The solid electrolyte body (substrate) of the instant oxygen sensing element may be formed of various known oxygen-ion conductive solid electrolyte materials. Preferably, the solid electrolyte body is formed of a fully or partially stabilized zirconia ceramic which includes a suitable stabilizing agent such as yttria ($Y_2O_3$), calcia (CaO), magnesia (MgO), or ytterbia ($Yb_2O_3$). The solid electrolyte material usually contains suitable sintering aids, for example, kaoline or other clays, $SiO_2$, $Al_2O_3$, and $Fe_2O_3$.

The selected solid electrolyte material is formed into a desired tubular shape in a suitable known process such as a press molding by using a rubber press, for example. Thus, an unfired formed body that gives by firing thereof a tubular solid electrolyte body of the sensing element is prepared.

If necessary, the unfired formed body is calcined as needed, at a temperature lower than a firing temperature at which the unfired formed body is fired. The above-indicated undulated portion is formed at least in a portion of the surface area of the unfired or calcined formed body on which the electrode is subsequently formed. This undulated portion is provided either by direct mechanical roughening of the appropriate area of the surface of the unfired or calcined formed body, for example, by sand blasting or by using a sand paper, or alternatively by spraying a slurry to the appropriate surface area of the formed body. The slurry may consist of a powdered mass principally consisting of an oxygen-ion conductive solid electrolyte material, and a binder and a solvent. The undulated portion may also be formed by dipping the unfired or calcined formed body in the slurry.

In the case where the undulated portion is provided in the form of an undulated layer formed on the surface of the unfired or calcined formed body, by the spraying or dipping method as indicated above, it is preferred that the solid electrolyte material for the slurry used to form the undulated layer has a higher degree of sinterability than that of the oxygen-conductive solid electrolyte material for the unfired or calcined formed body that gives the solid electrolyte body. Namely, the unfired undulated layer should be sintered at a firing temperature lower than the sintering temperature of the unfired or calcined formed body, so that the fired undulated layer advantageously has a dense structure with a comparatively low open porosity. The thus increased density of the undulated layer assures enhanced operating response of the sensing element, increased adhesive strength of the protective coating, increased strength of the solid electrolyte body, and improved bonding strength between the solid electrolyte body and the undulated layer.

The following techniques are available to change or adjust the sinterability of the solid electrolyte material for the unfired undulated layer formed on the solid electrolyte body. Namely, the sintering temperature of the unfired undulated layer can be lowered by using (a) a solid electrolyte material whose average particle size is smaller than that of the unfired solid electrolyte body, (b) a solid electrolyte material in the form of a dry-crushed powder, or (c) a zirconia ceramic which contains a smaller content of stabilizer than the material used for the solid electrolyte body. The sinterability of the solid electrolyte material for the undulated layer may also be improved by increasing the content of sintering aids included in the material. Further, it is noted that the sintering temperature of the solid electrolyte of the unfired or calcined formed body for the solid electrolyte body can be raised by lowering a forming pressure applied to the material when the unfired mass for the solid electrolyte body is formed under pressure, for example, on a rubber press or cold isostatic press. In other words, the sintering temperature of the solid electrolyte material for the undulated layer may be lowered with respect to the sintering temperature of the unfired or calcined formed body, by lowering the forming pressure of the formed body. The techniques indicated above are selectively used, either alone or in suitable combination.

The unfired or calcined formed body and the unfired undulated layer formed thereon are co-fired under the conditions which are selected for suitably sintering the unfired or calcined formed body. Thus, the fired solid electrolyte body of the oxygen sensing element is prepared, such that the undulated portion is formed at least in the portion of the surface area of the fired structure on which the electrode is subsequently formed.

In the case where the undulated portion is formed by co-firing the unfired undulated layer with the unfired or calcined formed body for the solid electrolyte body, the fired undulated layer is formed as an integral outer portion of the fired solid electrolyte body. Although the unfired undulated layer has a lower density than the formed body before the co-firing operation, the fired undulated layer is given almost the same density or open porosity as the fired solid electrolyte body, since the solid electrolyte material of the unfired undulated layer can be sintered better than that of the unfired or calcined formed body for the solid electrolyte body. In other words, the unfired undulated layer can be sintered at the same time when the unfired or calcined formed body is sintered. When the unfired undulated layer is sintered, the co-firing temperature is elevated to the sintering point of the unfired or calcined formed body. The higher sinterability and the denser structure of the undulated layer lead to effectively increased adhesive strength between the undulated layer and the solid electrolyte body, and also contribute to improving the solid electrolyte body.

BRIEF DESCRIPTION OF THE DRAWINGS

The above and optional objects, features and advantages of the present invention will become more apparent by reading the following detailed description of the invention, when considered in connection with the accompanying drawings, in which:

FIG. 2(a) is an elevational view partly in longitudinal cross section of the oxygen sensing element of FIG. 1;

FIG. 2(b) is a fragmentary enlarged view of a portion of the sensing element indicated at A in FIG. 2(a);

FIG. 2(c) is a view corresponding to that of FIG. 2(b), showing a modified form of a protective coating formed on the solid electrolyte body.

DETAILED DESCRIPTION OF THE INVENTION

Figures 1, 3:
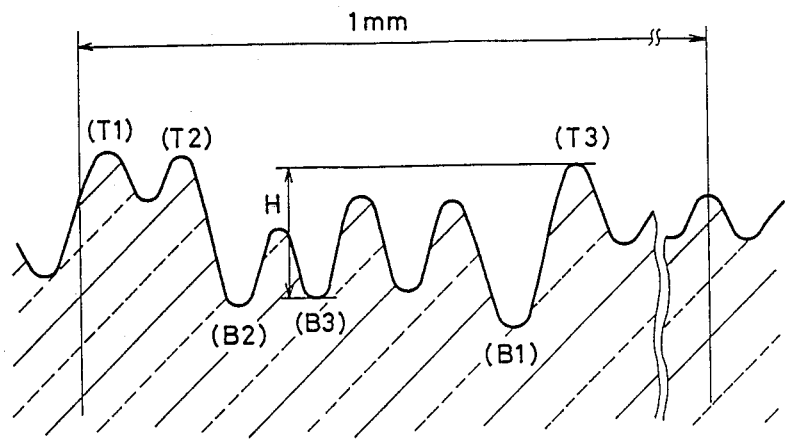
FIG. 1 is a fragmentary illustration in cross section of a solid electrolyte body of one embodiment of an oxygen sensing element of the invention, showing a manner of determining an average height of undulation on the surface of the solid electrolyte body.
FIG. 3 is a graph representing the result of a durability test of the illustrated sensing element of the invention, as compared with a comparative example without an undulated portion on the surface of its solid electrolyte body.

In the oxygen sensing element according to the invention, the undulated portion is formed at least in a portion of the surface area of the fired solid electrolyte body on which the electrode is disposed. Referring to FIG. 1, the undulated portion has an average height of at least 50 microns. This average height is determined by measuring a height H between the top of a third highest convexed part indicated at (T3) in the figure, and the bottom of a third deepest concaved part indicated at (B3) in the same figure. Described in greater detail, these third highest and deepest convexed and concaved parts are selected within a length of 1 mm as indicated in FIG. 1, by cutting the undulated portion in a longitudinal cross sectional plane, and observing the cut surface by an electronic or optical microscope. The height H is then measured. Usually, the average height of undulation of the undulated portion is determined by a mean value of the heights H measured at three different locations of the undulated portion along the length of the solid electrolyte body.

Then, at least the measuring and reference electrodes are formed on the solid electrolyte body on which the undulated portion is formed as described above. More specifically, the measuring electrode is formed or positioned such that at least a portion thereof which is particularly susceptible to a thermal damage due to hot measurement gas is formed on the undulated portion of the surface of the solid electrolyte body. The electrodes are provided as thin layers of a suitable metal selected from the platinum group, e.g., platinum, ruthenium, osmium, iridium, rhodium or palladium, or an electrically conductive material whose major component is selected from the platinum group. The electrodes may be formed in a suitable manner commonly practiced in the art, for example, by plating, sputtering, thermal decomposition of salts of the electrode metal, or firing of an applied paste of the electrode metal.

After the measuring electrode is thus formed on the undulated portion of the surface of the solid electrolyte layer, a porous ceramic protective coating is formed so as to cover the measuring electrode, for improving the durability of the measuring electrode. While this ceramic protective coating may be formed in various known methods, a generally practiced method is to use a plasma- or flame-spray coating technique. In particular, the plasma-spray coating is preferred. In this method, a selected ceramic material, usually spinel ($Al_2O_3$ MgO), is sprayed on the measuring electrode, by means of Ar/He, Ar/$N_2$ or $N_2$/$H_2$ plasma flame, so as to form a desired ceramic protective coating.

Since the measuring electrode is formed as an undulated layer following the undulation of the solid electrolyte body, and since the undulation has an average height of at least 50 microns, an inner portion of the porous ceramic protective layer is anchored in the concaved parts of the undulated measuring electrode layer, and is therefore firmly positioned within the corresponding concaved parts of the undulated portion of the solid electrolyte body. Consequently, the adhesive strength of the protective coating with respect to the solid electrolyte body is effectively increased, and the otherwise possible peel-off or separation of the protective layer can be avoided. Thus, the durability of the protective coating is enhanced, permitting the oxygen sensing element to operate with contemplated operating characteristics, for a sustained period of time. The thus prepared oxygen sensing element is built in the housing of an oxygen sensor.

It is preferred that the width of each concaved part of the undulated portion of the solid electrolyte body be greater than one third ($\frac{1}{3}$) of a height of the lower one of the corresponding two convexed parts adjacent to the concaved part involved. The thus determined width allows for sufficient anchoring of the porous ceramic protective coating to the concaved parts of the undulated portion of the solid electrolyte body, via the accordingly undulated measuring electrode. In this connection, the term "width" of the concaved parts is interpreted to mean a distance between the facing surfaces (as seen in FIG. 1) of each concaved part, as measured at a midpoint of the height of the above-indicated lower one of the two adjacent convexed parts.

The porous ceramic protective coating having a relatively high porosity is relatively difficult to be clogged. The porosity of the protective coating can be increased by reducing the energy consumed for the spray-forming of the coating, or by forming the coating of a ceramic material which is relatively difficult to fuse, for instance, zirconia (which melts or fuses at about 2500° C., as compared with a lower fusing point of about 2100° C. for spinel). The protective coating having such a relatively high porosity suffers from poor adhesion to the solid electrolyte body. According to the present invention, however, the undulated surface of the solid electrolyte body having height of 50 microns or more serves to prevent peel-off or flake-off of the porous protective coating, even if the porosity of the coating is relatively high. Stated differently, the undulation provided on the solid electrolyte body according to the present invention makes it possible to assure considerably increased durability of the protective coating, while at the same time maintaining a sufficiently high degree of porosity of the protective coating in order to avoid easy clogging of its porous structure.

Referring next to FIGS. 2(a) and 2(b), there is illustrated one embodiment of an oxygen sensing element of the present invention constructed and produced as described above. In FIG. 2(a), the oxygen sensing element is indicated generally at 2. The sensing element 2 has a tubular solid electrolyte body 4 which is made of a selected oxygen-ion conductive solid electrolyte material. The tubular solid electrolyte body 4 is closed at its one end and open at the other end, and has a measuring electrode formed in its outer surface, and a reference electrode formed in its inner surface. The measuring electrode is exposed to the measurement gas, while the reference electrode is exposed to a reference gas such as ambient air having a known oxygen concentration.

Described more specifically by reference to FIG. 2(b), the reference electrode indicated at 6 is formed on the inner surface of the tubular solid electrolyte body 4, while an undulated layer 8 is formed on the outer surface of the solid electrolyte body 4, as an integral part of the body 4. The measuring electrode, which is indicated at 10, is formed on the undulated surface of the undulated layer 8, i.e., on the undulated portion 8 of the solid electrolyte body 4. The measuring electrode 10 is covered by a porous ceramic protective coating 12, such that an inner portion of the coating 12 is positioned within concaved parts of the undulated layer 8 (more precisely, within the corresponding concaved parts of the undulated measuring electrode 10). The protective coating 12 has a suitable thickness.

While the entire area of the measuring electrode 10 shown in FIG. 2(b) is exposed to the measurement gas through the porous structure of the protective coating 12, it is possible that a portion of the measuring electrode 10 is left uncovered by the protective coating 12, as indicated at 14 in FIG. 2(c), so that the exposed areas 14 are exposed directly to the measurement gas. Since the protective coating 12 is formed by spraying a molten ceramic material against the undulated surface of the measuring electrode 10, and since the undulated surface has a height of at least 50 microns, preferably, at least 100 microns, the exposed areas 14 may be suitably provided on one of two flanks of some of the convexed parts of the undulated surface of the undulated layer 8, as illustrated in FIG. 2(c), or on the bottom of some of the concaved parts of the undulated surface, depending upon the direction in which the ceramic material for the protective coating 12 is sprayed. However, the exposed areas 14 of the measuring electrode 10 may be replaced by areas which are covered by a comparatively reduced thickness of the protective coating 12. It is noted that FIG. 2(c) is provided to illustrate the different locations of the exposed areas 14 of the measuring electrode 10, and is not interpreted to show the protective coating 12 which is practically formed. Namely, each exposed area (14) is formed on the same side of the corresponding convexed part of the undulated layer 8, if the spraying of the ceramic material is conducted in one direction.

It is recognized that the operating response of an oxygen sensing element is improved with an increase in the cumulative operating time, i.e., cumulative time of exposure to exhaust gases, due to the so-called "aging effect", while on the other hand the operating response during an initial period of use is relatively low. It is also noted that the operating response is eventually deteriorated due to clogging of the sensing element, after a long period of service. The exposed or slightly covered areas 14 of the measuring electrode 10 as described above are effective to improve the operating response of the oxygen sensing element even during an intial period of use. The aging effect may cause the covered areas of the measuring electrode 10 to enable the sensing element to maintain the intended operating response, by the time when the exposed areas 14 of the electrode 10 are heavily deteriorated. Thus, a variation in the operating response of the sensing element can be diminished by the provision of the exposed or slightly covered areas 14. Therefore, the instant oxygen sensing element, when used for automotive engines, for example, can facilitate adjustment of the engines, for compensating for an otherwise large variation in the response characteristic of the sensing element during its use.

Further, the areas of the measuring electrode 10 which are disposed within the bottoms of the concaved parts of the undulated layer 8 of the solid electrolyte body 4 are generally covered by a comparatively large thickness of the protective coating 12, and are therefore exposed to the measurement gas through the accordingly large thickness of the porous structure of the protective coating 12. For this reason, those areas of the electrode 10 are less likely to be deteriorated, and are capable of functioning to correctly determine an oxygen concentration of the measurement gas, even after the areas of the electrode 10 formed on the tops of the convexed parts of the undulated layer 8 are deteriorated. Thus, the variation in the operating characteristic of the sensor can be further reduced.

EXAMPLES

To further clarify the concept of the present invention, some typical examples of the invention will be illustrated and described. However, it is to be understood that the invention is by no means limited to the precise details of the illustrated examples, but may be embodied with various changes and modifications, which may occur to those skilled in the art, without departing from the spirit and scope of the present invention.

Initially, a small amount of clay as a sintering aid was well mixed with a solid electrolyte material which consists of 94 mole % of zirconia and 6 mole % of yttria. The obtained mixture was calcined at 1000° C. for three hours. The calcined mass was wet-crushed for 20 hours in a ball mill, whereby a high-viscosity slurry was prepared. Polyvinyl alcohol was added as a binder to the obtained slurry such that the polyvinyl alcohol was 1% by weight of the solid content of the slurry. Then, the slurry was processed by a spray drier, so as to prepare a solid electrolyte mass in the form of granules whose grain size is about 50 microns.

By using the thus prepared granular solid electrolyte mass, unfired tubular bodies as shown in FIG. 2(a) were formed by a rubber press. Further, unfired planar bodies were prepared from the same solid electrolyte mass.

The unfired tubular and planar formed bodies were subjected to one of the following processes (a) and (b), to undulate at least a portion of the surface of the unfired formed bodies on which the measuring electrode was subsequently formed.

(a) calcining the unfired formed bodies at 1200° C.; and undulating the appropriate portion of their surface by sand blasting.

(b) preparing a slurry which consists of the solid electrolyte mass wet-crushed by the ball mill as indicated above, polyvinyl alcohol (PVA) as a binder, and water as a solvent; and spraying the prepared slurry with a compressed air by a spray gun, against the appropriate portion of the surface of the unfired formed bodies.

The unfired formed bodies whose surfaces were undulated by one of the above two processes were fired at 1450° C. Thus, samples of a fired solid electrolyte body were prepared. The fired outer surface of each sample was found to have a comparatively uniform undulation, with orderly arranged convexed and concaved parts. Thus, each sample was provided with an integral undulated portion formed on its outer circumferential or flat surface.

Then, reference and measuring electrodes were formed on the inner and outer surfaces of each fired solid electrolyte body, respectively, by applying platinum by an ordinary plating method, and firing the formed platinum layers at 900° C.

Subsequently, powdered spinel was plasma-sprayed on the platinum measuring electrode formed on the undulated outer surface of the solid electrolyte bodies. Thus, a porous ceramic protective coating (12) was formed so as to cover the measuring electrode. On some of the solid electrolyte bodies, the protective coating (12) was formed with spraying power of 22 Kw, and by using the spinel powder whose grain size falls within a range of 10–50 microns or 20–90 microns. On the remaining solid electrolyte bodies, the protective coating (12) was formed with spraying power of 30 Kw, and by using the spinel powder whose grain size falls within the above-indicated 20–90 micron range. Thus, the protective coatings were formed under the three different conditions, as indicated in Table 2 which will be described. As described above, various samples of an oxygen sensing element were prepared.

MEASUREMENT OF OPERATING RESPONSE

The samples whose protective coating (12) was formed of the spinel powder of 10–50 grain size, with spraying power of 22 Kw, were tested for their operating response. To form the protective coating (12) on these samples, the following two different methods were used:

(1) Samples A:

The porous protective coating (12) of spinel was formed by spraying the spinel over the undulated surface of the platinum measuring electrode (10), in a direction that permits the measuring electrode (10) to be partially left uncovered by the protective coating (12), at its areas each of which corresponds to the same one of the two flanks or slopes of each convexed part of the undulated layer (8). That is, the spraying direction was selected to permit the measuring electrode (10) to have substantially exposed areas (14) on the flanks of the convexed parts of the undulated layer (8) which are on the same side. The exposed areas (14) may be covered by a very small thickness of the formed spinel coating (12).

(2) Samples B:

The porous protective spinel coating (12) was formed with a substantially uniform thickness over the entire undulated layer (8), by spraying the spinel in two different directions.

Oxygen sensors were prepared by using the sensing elements according to Samples A and B having the different protective coatings (12) formed on the undulated measuring electrode (10). The sensors were attached to an exhaust pipe of an internal combustion engine, such that the sensing elements were exposed to exhaust gases. An air-fuel mixture supplied to the engine was changed from a fuel-rich mixture to an air-rich mixture, so that the exhaust gases were changed from rich-burned exhaust gases to lean-burned exhaust gases. The operating response of each sensor was tested by measuring a time T between a moment when the exhaust gases were changed, and a moment when the output of the sensor was changed. The measured response times T of the tested sensors are indicated in Table 1.

It follows from Table 1 that the oxygen sensors using the sensing elements according to Samples A whose measuring electrode has the exposed or slightly covered areas (14) substantially directly exposed to the exhaust gases, exhibited shorter response times T, i.e., better operating response, than the sensors according to Samples B, while the sensors were substantially new.

TABLE 1

| Specimen No. | RESPONSE TIME (msec) | | | | | |
| --- | --- | --- | --- | --- | --- | --- |
| | 1 | 2 | 3 | 4 | 5 | Ave. |
| Samples A | | | | | | |
| While substantially new | 150 | 135 | 170 | 160 | 165 | 156 |
| After 300-hour use | 140 | 160 | 145 | 155 | 130 | 146 |
| Samples B | | | | | | |
| While substantially new | 180 | 190 | 155 | 180 | 195 | 180 |
| After 300-hour use | 140 | 155 | 140 | 170 | 125 | 146 |

DURABILITY TEST

Seven oxygen sensors using the oxygen sensing elements wherein the undulated layer (8) has an average height H of 50–60 microns were attached to the exhaust pipe of an engine (4-cylinder, 2000 cc displacement). Also, seven oxygen sensors using comparative sensing elements without an undulated layer were attached to the exhaust pipe of the same engine. The sensing elements according to the invention and the comparative sensing elements were exposed to exhaust gases of 700°–950° C., for 1000 hours, by operating the engine in a 30-minute cycling fashion, that is, operating the engine at 5000 rpm for 20 minutes, and at 2000 rpm for 10 minutes.

The result of the above durability test is illustrated in FIG. 3, which shows that the sensing elements having the undulated layer (8) according to the invention provided a sufficient output level even after a 1000-hour test operation, while the comparative sensing elements without an undulated layer on the outer surface of the solid electrolyte body became incapable of providing a sufficient output level before the 1000 hours of operation. That is, the durability of the comparative sensing elements were found unsatisfactory.

In the graph of FIG. 3, symbol "x" indicates the point of time in the test, at which the output of the sensing element dropped below 500 mV during combustion of a fuel-rich air-fuel mixture in the engine. On the other hand, symbol "o" indicates a sensor output above 500 mV even after the 1000-hour test operation.

PEEL-OFF TEST OF PROTECTIVE COATING

The undulated layers having different heights of undulation were formed on the outer surface of the tubular and planar solid electrolyte bodies of the test specimens, in the manner described above. The measuring electrodes were formed by plating platinum on the undulated surface of the solid electrolyte bodies, and the porous spinel protective coatings were formed by plasma-spraying on the platinum electrodes, as described above. The platinum electrodes of the test specimens were exposed to aqua regia, so as to dissolve the platinum electrodes. Then, the protective coatings were observed to determine whether the coatings peeled off. The test results of the different specimens are shown in Table 2.

To check the protective coatings for the peel-off condition, each of the tubular specimens was cut in parallel transverse planes spaced apart from each other by a distance of 2 mm in the longitudinal direction of the tubular solid electrolyte bodies, whereby annular test pieces including an undulated outer surface were prepared. A portion of each annular test piece was removed, so that the electrode portion was exposed to aqua regia. Then, the protective coating was observed for the occurrence of peel-off or flake off. For the planar specimens, the platinum electrodes as formed on the solid electrolyte bodies were exposed to aqua regia, and the protective coatings were observed.

Table 2 shows the number of the test pieces of each specimen (consisting of ten pieces), which suffered from peel-off of their protective coating. It follows from Table 2 that the protective coatings of the specimens according to the present invention exhibited excellent adhesive strength, and were held securely adhering to the surface of the solid electrolyte bodies, even after the platinum electrodes were removed. This superior result is considered to be derived from the undulated outer surface of the solid electrolyte bodies, which has a height of undulation of at least 50 microns between the top of the convexed parts, and the bottom of the concaved parts in which the inner portion of the protective coatings is positioned for anchoring to the solid electrolyte body.

TABLE 2

| | | Number of Test Pieces (Out of 10 pcs.) Whose Protective Coatings Peeled Off | |
|---|---|---|---|
| Plasma-Spraying Power | | 22 Kw | 30 Kw |
| Grain Size of Spinel | | 10–50 μm | 20–90 μm |
| Specimens | | | |
| Undulation Height (μm) | Tubular/ Planar | | |
| 3–15 | Tubular | 10 | 10 | 8 |
| | Planar | 9 | 10 | 10 |
| 15–30 | Tubular | 3 | 6 | 4 |
| | Planar | 5 | 7 | 5 |
| 30–40 | Tubular | 1 | 2 | 0 |
| | Planar | 3 | 3 | 2 |
| 40–50 | Tubular | 1 | 1 | 0 |
| | Planar | 0 | 2 | 1 |
| 50–65 | Tubular | 0 | 0 | 0 |
| | Planar | 0 | 0 | 0 |
| 65–80 | Tubular | 0 | 0 | 0 |
| | Planar | 0 | 0 | 0 |
| 80–100 | Tubular | 0 | 0 | 0 |
| | Planar | 0 | 0 | 0 |
| 100–170 | Tubular | 0 | 0 | 0 |
| | Planar | 0 | 0 | 0 |

TABLE 2-continued

| | Number of Test Pieces (Out of 10 pcs.) Whose Protective Coatings Peeled Off | | |
|---|---|---|---|
| Planar | 0 | 0 | 0 |

As is apparent from the foregoing description, the outer surface of the solid electrolyte body of the oxygen sensing element constructed according to the present invention has an undulated portion on which the measuring electrode exposed to a measurement gas is formed. The undulated portion has an average height of at least 50 microns, which assures an improved operating response of the sensing element, and an increased resistance to peeling or separation of the protective coating which covers the measuring electrode.

What is claimed is:

1. An oxygen sensing element adapted primarily to determine an oxygen partial pressure of a measurement gas, comprising:

a solid electrolyte body formed of an oxygen-ion conductive solid electrolyte material, said body having a surface with at least a portion of which is undulated, said undulated portion having convexed and concaved parts;

an electrode deposited on said undulated portion of said surface of said solid electrolyte body; and a porous protective coating covering said electrode, such that said electrode is exposed to said measurement gas through said porous protective coating;

wherein said undulated portion of the solid electrolyte body has an average height of at least 50 microns between said convexed and concaved parts, each of said concaved parts has a width which is greater than one third of a height of a lower one of two corresponding convexed parts adjacent to said each concave part, as measured from a bottom of said each concaved part, and at least a portion of said porous protective coating is positoned within at least one of said concaved parts of said undulated portion of the solid electrolyte body.

2. An oxygen sensing element according to claim 1, wherein said solid electrolyte body consists of a tubular solid electrolyte body which is closed at one of opposite ends thereof and open at the other end, said tubular solid electrolyte body having an inner circumferential surface and an outer circumferential surface on which an undulated layer is formed as said undulated portion, said electrode being formed as a measuring electrode on said undulated layer and another electrode being formed as a reference electrode on said inner circumferential surface.

3. A method of producing an oxygen sensing element which includes a solid electrolyte body formed of an oxygen-ion conductive solid electrolyte material, and an electrode deposited on a surface of said solid electrolyte body, said method comprising the steps of:

preparing an unfired shaped body which provides said solid electrolyte body upon firing thereof, or a calcined shaped body obtained by firing said unfired shaped body at a temperature lower than a firing temperature of said unfired shaped body, said unfired or calcined shaped body being formed such that an undulated portion having convexed and concaved parts is formed at least in a portion of an area of the surface of said shaped body on which said electrode is deposited;

firing said unfired or calcined shaped body into said solid electrolyte body so that said undulated portion has an average height of at least 50 microns between said convexed and concaved parts, and each of said concaved parts has a width which is greater than one third of a height of a lower one of two corresponding convexed parts adjacent to said each concaved part, as measured from a bottom of said each concaved part;

depositing said electrode on said area of the surface of the prepared solid electrolyte body which includes said undulated portion; and forming a porous protective coating so as to cover said electrode, such that at least a portion of said protective coating is positioned within at least one of said concaved parts of said undulated portion of said solid electrolyte body.

4. A method according to claim 3, wherein said ion-conductive solid electrolyte material consists of zirconia which is fully or partially stabilized by a stabilizing agent.

5. A method according to claim 3, wherein said porous protective coating is formed by plasma-spraying a ceramic material over said electrode.

6. An oxygen sensing element adapted primarily to determine an oxygen partial pressure of a measurement gas, comprising:

a solid electrolyte body formed of an oxygen-ion conductive solid electrolyte material, said body having a surface with at least a portion of which is undulated, said undulated portion having convexed and concaved parts;

an electrode deposited on said undulated portion of said surface of said solid electrolyte body; and a porous protective coating covering a portion of said electrode, such that the portion of said electrode which is covered by said porous protective coating is exposed to said measurement gas through said porous protective coating and the portion of said electrode which is not covered by said porous protective coating is directly exposed to said measurement gas;

wherein said undulated portion of the solid electrolyte body has an average height of at least 50 microns between said convexed and concaved parts, and at least a portion of said porous protective coating is positioned within at least one of said concaved parts of said undulated portion of the solid electrolyte body.

7. An oxygen sensing element according to claim 6, wherein said oxygen-ion conductive solid electrolyte material consists of zirconia which is fully or partially stabilized by a stabilizing agent.

8. A method of producing an oxygen sensing element which includes a solid electrolyte body formed of an oxygen-ion conductive solid electrolyte material, and an electrode deposited on a surface of said solid electrolyte body, said method comprising the steps of:

preparing an unfired shaped body which provides said solid electrolyte body upon firing thereof, or a calcined shaped body obtained by firing said unfired shaped body at a temperature lower than a firing temperature of said unfired shaped body, said unfired or calcined shaped body including an undulated portion having convexed and concaved parts formed at least in a portion of an area of the surface of said shaped body on which said electrode is deposited, said undulated portion being formed on said unfired or calcined shaped body by spraying a slurry on said portion of said area of the surface of said unfired or calcined formed body, said slurry including a powdered mass consisting essentially of an oxygen-ion conductive solid electrolyte material, a binder, and a solvent;

firing said unfired or calcined shaped body into said solid electrolyte body so that said undulated portion has an average height of at least 50 microns between said convexed and concaved parts;

depositing said electrode on said area of the surface of the prepared solid electrolyte body which includes said undulated portion; and forming a porous protective coating so as to cover said electrode, such that at least a portion of said protective coating is positioned within at least one of said concaved parts of said undulated portion of said solid electrolyte body.

9. A method according to claim 8, wherein said undulated portion is formed by roughening, by sand blasting, said portion of said area of the surface of said unfired or calcined shaped body.

* * * * *